United States Patent
Nehmi Filho

(10) Patent No.: US 10,973,245 B2
(45) Date of Patent: Apr. 13, 2021

(54) IMMUNOMODULATORY AND GROWTH PROMOTING AND CONTROLLING COMPOSITION OF INTESTINAL MICROBIOTA UNDESIRABLE BACTERIA AND ITS USE

(71) Applicant: YESSINERGY HOLDING S/A, Campinas (BR)

(72) Inventor: Victor Abou Nehmi Filho, São Paulo (BR)

(73) Assignee: YESSINERGY HOLDING S/A, Sao Paulo (BR)

( * ) Notice: Subject to any disclaimer, the term of this patent is extended or adjusted under 35 U.S.C. 154(b) by 30 days.

(21) Appl. No.: 16/311,503

(22) PCT Filed: Jun. 9, 2017

(86) PCT No.: PCT/BR2017/050150
§ 371 (c)(1),
(2) Date: Dec. 19, 2018

(87) PCT Pub. No.: WO2017/219106
PCT Pub. Date: Dec. 28, 2017

(65) Prior Publication Data
US 2019/0261651 A1    Aug. 29, 2019

(30) Foreign Application Priority Data

Jun. 24, 2016   (BR) .................. 10 2016 014961-4
May 22, 2017   (BR) .................. 10 2017 010683-7

(51) Int. Cl.
| | | |
|---|---|---|
| A23K 20/163 | (2016.01) | |
| A61K 47/54 | (2017.01) | |
| A61K 31/7016 | (2006.01) | |
| A61K 31/702 | (2006.01) | |
| A61K 31/716 | (2006.01) | |
| A61K 31/736 | (2006.01) | |
| A61K 36/06 | (2006.01) | |
| A61K 36/064 | (2006.01) | |
| A61K 31/733 | (2006.01) | |

(52) U.S. Cl.
CPC .......... *A23K 20/163* (2016.05); *A61K 31/702* (2013.01); *A61K 31/7016* (2013.01); *A61K 31/716* (2013.01); *A61K 31/733* (2013.01); *A61K 31/736* (2013.01); *A61K 36/06* (2013.01); *A61K 36/064* (2013.01); *A61K 47/54* (2017.08)

(58) Field of Classification Search
None
See application file for complete search history.

(56) References Cited

U.S. PATENT DOCUMENTS

| | | | | |
|---|---|---|---|---|
| 7,883,874 | B2* | 2/2011 | Gibson ............... | A61P 1/00 435/101 |
| 8,753,668 | B2* | 6/2014 | Sedmak ............. | A61K 8/73 424/442 |
| 2002/0061345 | A1 | 5/2002 | Vuorenmaa et al. | |
| 2011/0189148 | A1* | 8/2011 | Ritter ................ | A23C 9/1234 424/93.45 |
| 2012/0121621 | A1 | 5/2012 | Jaszberenyi et al. | |
| 2014/0200266 | A1* | 7/2014 | Reed ................. | A61K 31/353 514/456 |

FOREIGN PATENT DOCUMENTS

| | | | | |
|---|---|---|---|---|
| BR | PI0417188 | A | 3/2007 | |
| BR | PI0910480 | A2 | 7/2015 | |
| CN | 103039700 | A * | 4/2013 | |
| CN | 104982744 | A * | 10/2015 | |
| GB | 2526242 | A * | 11/2015 | .......... A61K 31/716 |
| JP | S61199752 | U | 12/1986 | |
| JP | H10215790 | A | 8/1998 | |
| JP | H10276740 | A | 10/1998 | |
| WO | WO-0008948 | A2 | 2/2000 | |
| WO | WO-2012021783 | A2 | 2/2012 | |
| WO | WO-2013142792 | A1 | 9/2013 | |
| WO | WO-2016122887 | A1 | 8/2016 | |
| WO | WO-2017027601 | A1 | 2/2017 | |
| WO | WO-2017083520 | A1 | 5/2017 | |

OTHER PUBLICATIONS

Cardelle-Cobas et al (International Journal of Food Microbiology 149 (2011) 81-87.*
Yeast Derivatives Aug. 20, 2002 retrieved from https://www.ams.usda.gov/sites/default/files/media/Yeast%20Derivatives%20report.pdf.*
Khanvilkar et al. Agro Food Industry Hi Tech vol. 26(6) Nov./Dec. 2015.*
Dominguez et al. Food Bioprocess Technol DOI 10.1007/s11947-013-1221-6 2013.*
"International Application Serial No. PCT/BR2017/050150, International Search Report dated Sep. 5, 2017", w/ English Translation, (Sep. 5, 2017), 9 pgs.

(Continued)

*Primary Examiner* — Oluwatosin A Ogunbiyi
(74) *Attorney, Agent, or Firm* — Schwegman Lundberg & Woessner, P.A.

(57) ABSTRACT

This invention relates to a composition for additives which can be employed in animal feeds, or as growth promoters, or as nutraceuticals, or as prebiotics, or as additives for the control and prophylaxis of pathogenic bacteria in the intestinal tract of animals or farmed animals. An immunomodulatory and promoter composition for controlling the population of undesirable bacteria of the intestinal microbiota, comprising the components indicated below:
(a) Fructooligosaccharides (FOS);
(b) Galacto-oligosaccharides (GOS);
(c) Mannan-oligosaccharides (MOS);
(d) 1,3 and 1,6 Beta-glucans.

7 Claims, No Drawings

(56) References Cited

OTHER PUBLICATIONS

"International Application Serial No. PCT/BR2017/050150, Written Opinion dated Sep. 5, 2017", (Sep. 5, 2017), 5 pgs.

* cited by examiner

IMMUNOMODULATORY AND GROWTH PROMOTING AND CONTROLLING COMPOSITION OF INTESTINAL MICROBIOTA UNDESIRABLE BACTERIA AND ITS USE

PRIORITY APPLICATIONS

This application is a U.S. National Stage Filing under 35 U.S.C. 371 from International Application No. PCT/BR2017/050150, filed on Jun. 9, 2017, and published as WO2017/219106 on Dec. 28, 2017, which claims the benefit of priority to Brazilian Application No. 10 2017 010683-7, filed on May 22, 2017 and to Brazilian Application No. 10 2016 014961-4, filed on Jun. 24, 2016; the benefit of priority of each of which is hereby claimed herein, and which applications and publication are hereby incorporated herein by reference in their entirety.

FIELD OF INVENTION

This invention relates to a composition for additives which can be employed in animal feeds, or as growth promoters, or as nutraceuticals, or as prebiotics, or as additives for the control and prophylaxis of pathogenic bacteria in the intestinal tract of animals or farmed animals.

BACKGROUND ART

The intestinal microbiota consists of a complex of several species of microorganisms, which live in the intestinal tract, mainly in the large intestine, reaching approximately $1.10^{13}$ cells, making it the largest reservoir of microorganisms in both animals and humans. Among the benefits that the microbiota can give to the host is the greater use of energy and nutrients from food, since they are not fully digested and absorbed during the passage through the gastric system, and may still contain many nutrients when they reach the intestinal tract. Fermentation, one of the major benefits of undigested carbohydrates fermented in the large intestine, is to promote the formation and subsequent absorption of short chain fatty acids. Among these short chain fatty acids, the most important are the butyric acid, which is metabolized by the intestinal colon epithelium, the propionic acid, which is metabolized by the liver and used as a substrate for production of glucose in the process of gluconeogenesis, and the acetic acid, which is absorbed from muscle tissue and other tissues, and used as an energy source. In addition, intestinal bacteria also synthesize vitamin B and vitamin K. Human and domestic animal bodies carry around trillions of microorganisms in their intestines and not all species have been identified, varying greatly from subject to subject. Most of the bacteria belong to the genera *Bacteroides, Clostridium, Fusobacterium, Eubacterium, Ruminococcus, Peptococcus, Peptostreptococcus*, and *Bifidobacterium*. Genres such as *Escherichia* and *Lactobacillus* are present to a lesser extent. In addition to bactéria, fungi are also present, which include *Candida, Saccharomyces, Aspergillus*, and *Penicillium*. The Archaea is another great microbial class present in the intestinal microbiota.

As already mentioned, the bacteria in the intestinal microbiota fulfill several useful and beneficial roles to hosts, whether humans or animals, which include, among them, the ability to metabolize non-digestible saccharides, regulate lipid metabolism, and biosynthesize vitamins. However, this benefit goes much further, since the existence of a beneficial microbial population works by stimulating cell growth, suppressing the growth of harmful microorganisms, training the immune system to respond only to pathogens, and promoting the defense against some diseases. Pathogens can cause undesirable pathologies, besides representing a trend to allergies caused by excessive reactions of the immune system, due to the predominance of *C. difficile* and *S. aureus*, and the lower predominance of beneficial microorganisms such as *Bacteroides* and *Bifidobacterium*.

*Salmonella* is a genus of bacteria commonly called salmonellae, which belong to the Enterohacteriaceae family. They are gram-negative, rod-shaped bacteria, mostly mobile (with periurachal flagella), non-sporulated, encapsulated, having fimbriae, most of which do not ferment lactose. Salmonellae are an extremely heterogeneous genus, composed of three species, *Salmonella subterranea, Salmonella bongori* and *Salmonella enterica*, the latter with about 2,610 serotypes.

The intestinal tract of man and animals is the main natural reservoir for this pathogen, with bird-origin food being important transmission routes.

The most important to human health are *Salmonella typhi* (*Salmonella enterica* serovar *Typhi*) that causes systemic infections, typhoid fever and endemic disease in many developing countries, and *Salmonella Typhimurium* (*Salmonella enterica* serovar *Typhimurium*) and *Salmonella Enteritidis* (*Salmonella enterica* serovar *Enteritidis*) is the most common cause of salmonellosis-type gastroenteritis, transmitted by food to humans.

*Escherichia coli* is a Gram-negative, facultative anaerobic bacillus, and do not produce spores. They have fimbriae or adhesins that allow their fixation, preventing them from being washed out through urine or diarrhea. They are part of the human microbiota and are mostly non-pathogenic. However, some strains are considered pathogenic for producing enterotoxins. They have lipopolysaccharide (LPS), like most Gram-negative bacteria, which disproportionately activate the immune system and excessive vasodilatation caused by the cytokines produced, which can lead to septic shock and death in cases of septicemia.

The number of people infected with *E. coli* has increased year by year. Excessive use of antibiotics, even at levels that promote growth in animal production for human consumption, has led to the emergence of large populations of pathogenic microorganisms, resistant to antibiotics.

Antibiotics are the oldest and most successful substance used for the manipulation of the intestinal microbiota. When used in sub-dosages, they eliminate only the most sensitive individuals from some unwanted species of bacteria in the intestinal microbiota. As these subjects are eliminated, a greater efficiency in the feed conversion is achieved. That is a higher animal weight production with the same amount of food. For this reason, they are known as growth-promoting antibiotics, or GPAs. The disadvantage of this application is that the use in sub-doses promotes microbial resistance to the active principle, selecting only resistant microorganisms, which can be a very serious public health aggravating factor. This is because the resistance characteristic given by the genes of these microorganisms can be transmitted from one microorganism to another, reaching even the population of the human microbiota through the consumption of contaminated food.

In 2006, the European Union began to ban the use of antibiotic growth promoters used in animal feed. The United States also decided to ban the use of antibiotic growth promoters in animal feed from January 2017.

To date, much of the replacement of growth-promoting antibiotics has been made by short-chain organic acids, especially butyric acid. In addition to them, essential oils, tannins, and other bactericidal substances have also been used. However, they can produce side effects in animals, such as chronic headaches and heartburn. In addition, unique bactericidal substances, such as those mentioned, have a great chance of going through the same process of selection of "resistant" subjects, as is happens with antibiotics. There are already signs of adaptation of certain species and serotypes of *Salmonella* and *E. coli*, which are also becoming resistant to organic acids, showing that the replacement of growth-promoting antibiotics requires more complex products that attack harmful bacteria on several fronts and through different modes of action, to prevent them from becoming resistant to the product.

Among the several possible fronts for attacking undesirable bacteria, such as *Salmonella* and *E. coli*, are the prebiotics agglutination bacteria, like MOS (Mannan-Oligosaccharides), immune modulators such as Beta-glucans and prebiotics that promote competitive exclusion, such as that caused by the bifidogenic effect of prebiotics such as FOS (Fructooligosaccharides) and GOS (Galacto-oligosaccharides), among others. The best thing would be to ally these 3 fronts of attack in one single product.

Synergy between these compounds, MOS, Beta-glucans, FOS and GOS (among other prebiotics that has a bifidogenic effect) contribute to a greater diversity and greater predominance of populations of beneficial bacteria in the intestinal microbiota, which hinders the proliferation of pathogens. This beneficial population diversity operates on 3 major fronts, i.e., through 3 different mechanisms of action. First, as a direct antagonism or competitive exclusion, by which beneficial or probiotic bacteria will produce bioactive peptides, as well as bacteriocins with antimicrobial activity. Through these defense mechanisms, the beneficial bacteria gain space to expand their populations, to the detriment of the spaces occupied by the undesirable bacteria. Prebiotics like FOS and GOS are saccharides fermentable only by certain beneficial bacteria. Due to the use of these sugars selectively, beneficial bacteria produce organic acids, which decrease intestinal pH, increase the epithelial barrier and reduce the possibility of pathogen adhesion to it. To prove this effect, studies with *Lactobacillus acidophilus* and *salivarium* show their activity against the bacteria of the genera *Listeria* and *Salmonella* (Preidis et al, 2011). Second, with the immunomodulatory action, which is promoted by both the beneficial bacteria and the Beta-glucans, by activating the innate and adaptive immune system. Beta-glucans stimulate the production of macrophages and their phagocytosis activity, including undesirable bacteria that adhere to the intestinal walls or invade the lymphatic system. In addition, we have the production of short chain fatty acids, which are products of the metabolism of beneficial bacteria, which send signals to the brain to "feed" the immune system. Among these fatty acids, butyric acid is the main acid metabolized by the intestinal epithelium, which acts by stimulating the process of apoptosis and the production of protective mucus that is very important to maintain the integrity of the intestinal walls. And third, with the mechanism of bacteria agglutination by the MOS. Manoses contained in MOS permanently adhere to the adhesins of type 1 fimbriae of bacteria of the genera *Salmonella* and *E. coli*, preventing them from attaching to the intestinal walls and causing enteritis. This is a mechanism of physical attraction that, depending on the quality of the MOS, can agglutinate with a reasonable intensity most of the varieties and serotypes of these undesirable bacteria.

The agglutinating effect of bacteria harboring type 1 fimbriae promoted by MOS can be considered a physical attack against these bacteria. In practice, the action of MOS can be understood as that of a physical trap to capture these bacteria in the digestive tract. Therefore, they are prevented from attaching to the walls of the intestine and causing enteritis, of which scarring calluses reduce the nutrient absorption capacity of the intestine.

The immunomodulatory effect of beta-glucans can be considered a physiological attack of the organism against these harmful bacteria. It is manifested in the form of faster healing of enteritis produced on the walls of the intestine by these bacteria, allowing a quick overlay of these walls by the protective mucus.

The competitive exclusion produced by prebiotics having a bifidogenic effect, as FOS and GOS, can be considered a chemical and environmental attack against undesirable bacteria, especially *Salmonella*, and *E. coli*, *Clostridium* and others. It occurs by multiplying the populations of desirable bacteria, mainly of the genera *Lactobacillus* and *Bifidobacterium*, at the end of the intestinal tract. The bacteria of these genera are acidogenic, so causing an increase in the acidity of the intestinal tract, which is intolerable for undesirable bacteria that inhabit this region of the digestive tract, especially *Salmonella* and *E. coli*. In addition, these beneficial bacteria produce bacteriocins and other bioactive peptides, which act as natural antibiotics.

Therefore, the urgent replacement of animal feed antibiotics with prophylactic additives of pathogens in the human and animal microbiota indicates that one of the possibilities is the use of prebiotics in animal feed.

Prebiotics are defined as non-digestible food ingredients that benefit health as they stimulate the growth or activity of beneficial bacteria in our colon or intestinal tract.

Fructooligosaccharides (FOS) and galacto-oligosaccharides (GOS) are the most extensively studied prebiotics and have a proven bifidogenic effect.

Fructooligosaccharides or FOS are prebiotics which is also called oligofructose or oligofrutans, since they are the fructose oligosaccharides that can be used as sweeteners. They emerged in the 1980s as a response to consumers' tendency to employ low-calorie sweeteners. Commercially produced Fructooligosaccharides (FOS) are obtained by the extraction and hydrolysis processes of the inulin molecule present in many plants and by the enzymatic reaction of transfructosylation of the sucrose molecule. Inulin is a fructose polymer, or polyfructose, with a degree of polymerization of from 10 to 60. Inulin can also be hydrolyzed into smaller molecules by chemical and enzymatic methods, generating blends of oligosaccharides with the general structure Glucose-Fructose or Gli-Fru$_n$ (abbreviation GF$_n$) and Fru$_m$ (F$_m$), with n ranging from 2 to 9 and IV ranging from 2 to 10. This process occurs naturally in nature, so these oligosaccharides can also be found in many vegetables such as artichoke, chicory, and agave. The compositions of the commercial products may comprise kestose (GF2), nistose (GF3), fructofuranosyl-nistose (GF3), inulobiose (F2), inulotriose (F3) and inulotetraose (F4). The second type of FOS is obtained by transfructosylation by p-fructofuranosity (invertase) and fructosyltransferase enzymes present in many microorganisms, such as *Aspergillus niger, Aspergillus* sp., *Aureobasidium* sp. This process generates a mixture of the general formula GF$_n$, with n ranging from 1 to 5. All these isomers and oligomers are called FOS.

In vitro propagation studies show that the higher the concentration of short-chain polymers in FOS, i.e., the smaller n in the GF$_n$ general formula, the greater the bifidogenic effect of FOS. This means that FOS composed of short-chain polymer chains, such as GF2, GF3, and GF4, cause a larger population growth of bacteria of the genus *Lactobacillus* and *Bifidobacteria*.

Because their molecular conformation contains glycosidic linkages, fructooligosaccharides resist hydrolysis by enzymes of the gastrointestinal system and gastric juice and bile salts. In the colon, they are fermented by anaerobic bacteria. They represent low-calorie food and still contribute to the dietary fiber fraction.

FOS and inulin are present in many plants and foods such as blue agave, banana, onion, chicory, garlic, asparagus, yacon, honey, leeks, as well as grains and cereals such as wheat and barley. The highest concentrations of FOS are found in chicory, artichoke, yacon, and blue agave.

In Japan, since 1990, FOS has been recognized as an important prebiotic, capable of increasing the health of the gastrointestinal tract and has been proposed as a supplement for the treatment of fungal infections.

Many studies show that FOS and inulin promote increased absorption of calcium, and other minerals such as magnesium in the small intestine. This occurs due to the fermentation of these sugars by the microbiota, resulting in a lower pH or acid. As they are the most soluble minerals in acid pH, they allow a better use by the organism, so they can be better assimilated to enter the bloodstream.

Galacto-oligosaccharides (GOS) are known as oligogalactosylactose, oligogalactose, lactulose, oligolactose or transgalacto-oligosaccharides (TOS), and belong to the class of bifidogenic prebiotics as well. The composition of the galacto-oligosaccharide (GOS) fractions varies according to the chain length and type of bonds, between the monomer units. In general, they are produced by the enzymatic conversion of lactose, a component of bovine milk, by the enzyme β-galactosidase. But they can also be produced by chemical isomerization of lactose, as is the case of lactulose and are naturally present in soybeans.

GOS generally comprises a chain of galactose units resulting from transgalactosylation reactions, with a terminal glucose unit. However, the degree of GOS polymerization may vary markedly, ranging from 2 to 9 monomer units depending on the type of β-galactosidase enzyme used. The GOS molecules present in soybean differ from the GOS produced enzymatically because they are alpha-galacto-oligosaccharides. Among them are raffinose, stachyose, verbascose, and melibiose. They comprise galactose molecules attached to the sucrose molecules by a-1,6-type bonds. However, in the same way as the other class, they are also resistant to the enzymes of the gastrointestinal system and are fermented by the intestinal bacteria.

For birds and fish, i.e., for non-mammals, lactose itself is considered a prebiotic with bifidogenic effect and is covered by the designation GOS. The reason is that non-mammals do not produce lactase, which is the enzyme capable of digesting lactose, which allows it to reach intact the large intestine and be fermented by the bacteria of the genus *Lactobacillus* and *Bifidobacteria*. The "prebiotic" effect of lactose is explained by the fact that bacteria of the genus *Salmonella* do not metabolize lactose, whereas the genus *Lactobacillus* and *Bifidobacteria* do, indirectly provoking the 3 mechanisms of action incited by them, as already mentioned.

Also due to the glycosidic bonds present in the GOS, they are widely resistant to hydrolysis by saliva and enzymes of the digestive tract or intestine, therefore reaching almost the end of the large intestine, practically intact. The human intestine contains about 300 to 500 different bacterial species types, which can be divided into beneficial, such as *Bifidobacterium* and *Lactobacillus*, and harmful, such as *Clostridium, Salmonella*, and *Escherichia coli*, for example. Galacto-oligosaccharides or GOS, because they are prebiotics defined as nondigestible food ingredients that benefit the host bacteria, stimulate their growth and activities in the colon. One of the ways to aid health is that they produce organic acids through their fermentations. In short, they inhibit the growth of harmful bacteria, stimulate immune functions and the absorption of essential nutrients and the synthesis of certain vitamins.

Studies indicate that GOS supports much to improve the absorption of Calcium in the intestinal tract of humans and animals, and there are indications of the possibility of improving the absorption of Magnesium.

Interest in the use of mannan-oligosaccharides (MOS) to improve gastrointestinal health began in the 1980s. Scientists at the time found that the MOS mannose inhibited infections caused by *Salmonella*. Studies have shown that *Salmonella* can bind to mannose by projections of type 1 fimbriae, therefore reducing the risks of pathogenic colonization in the intestinal tract. Different types of mannose sugars interact differently with type 1 fimbriae. The form present on the walls of *Saccharomyces cerevisiae* cells (branched maims alpha-1,3 and alpha-1,6) are effective in the pathogenic connections. When they bind to mannose, the bacteria are physically and definitively captured by the MOS-containing particles and loaded out of the digestive tract along with the fecal bolus. The way of measuring the efficiency of each MOS source is by the amplitude and intensity of agglutination, for the several species and serotypes of Salmonellae and *E. coli*.

MOS is particularly important for animals, since intestine health allows a better absorption of the feed components. For many decades, antibiotics have been added to the composition of animal feeds in non-therapeutic prophylactic levels to prevent disease, to improve the feed conversion rate of feeds and to accelerate growth, therefore increasing the profitability of animal farmers. Today, there is a worldwide trend that desires to prevent this management, because it greatly increases the number of bacteria resistant to antibiotics, which are transmitted and can cause serious risks for humans. This fact has fueled interest in the development of functional foods, with MOS being among the main prebiotics capable of replacing antibiotics in animal feeds. Studies have shown that MOS impairs bacterial fixation in the intestinal wall of chickens, pigs and laying hens, and the reduction in the prevalence and concentration of several types of *Salmonella* (causing zoonosis in animals whose symptoms are diarrhea) as well as *Escherichia coli* (*E. coli*), *Clostridium*, among others. Researchers also found that MOS provokes increased mucus production by protecting intestinal microvilli in animals.

β-glucans comprise a group of β-D-glucose polysaccharides that occur naturally in the walls of cereal, yeast, bacterial and fungal cells, exhibiting different physicochemical properties depending on their source.

Typically, β-glucans have a linear structure with 1,3 β-glycosidic type bonds, ranging in their molecular weights, solubility, viscosity, branching, gelling properties, therefore causing several effects on animal physiology.

Several studies report the potential health effects of β-glucans. Oat fibers containing β-glucans, when ingested daily by at least 3 g, can lower levels of saturated fats in the blood and reduce the risk of heart disease. Other studies indicate that cereals containing β-glucans, such as oats can also act as immunomodulators, and act as food/ingredients that can lower cholesterol. β-glucans can be used as nutraceuticals, texturizing agents in cosmetics, supplements of soluble fibers, among others.

β-glucans represent arrangements on the six sides of the D-glucose rings connected linearly at each position carbon, varying from the source, although most commonly β-glucans include glycosidic bonds of type 1,3 in their structure. Although theoretically β-glucans are D-glucose polysaccharides linked by β-type glycosidic bonds, not all β-D-glucose polysaccharides are categorized as β-glucans. For example, cellulose is not a typical β-glucan because it is insoluble and does not exhibit the same physical and chemical properties of other cereal or oat β-glucans. β-glucans can present ramifications composed by proteins like the case of Polysaccharide-K.

Beta-glucans and mannans are part of the cell wall structure of yeast and fungi. For the industrial extraction of these elements and production of probiotics, the most common and desirable are those extracted from yeasts of the genera *Saccharomyces* and *Candida*.

JPS 61199752 document uses a culture of polished rice inoculated with *Atereobasidium* strains to obtain food enriched with Fructooligosaccharides and beta-1,3-1,6-glucans.

US 2002061345 document relates to a process for obtaining a poultry feed additive for the prevention of gastric disorders or intestinal diseases comprising filtration of beer yeast raw material containing oligosaccharides and polysaccharides and may also contain beta-glucans.

JPH 10215790 document of 1997 teaches the use of oligosaccharides as MOS, FOS, GOS; and acidifying agents such as propionic acid, formic acid, and citric acid, as well as bacteria producing lactic acid, butyrate, and *Bifidobacteria*, in feed undergoing heat treatment.

JPH 10276740 document of 1997 teaches the preparation of food or beverage containing beta-1,3-1,6-glucans, obtained from an *Aureobasidium* solution containing Fructooligosaccharides.

WO 0008948 document relates to a carbohydrate blend for dietary or pharmaceutical foods having component (A) in 90% of the blend, which may comprise oligosaccharides having 2 to 6 units or monosaccharides; and component (B), composed of polysaccharides containing more than 7 units, representing 10% of the total blend, 80 to 100% of (A) being GOS, and 80 to 100% of the carbohydrate (B) being FOS.

WO 2012021783 and WO 2013142792 documents address the dry stabilized composition of biological material containing carbohydrates and proteins comprising hydrolyzed proteins, the carbohydrates being polysaccharides, oligosaccharides, or disaccharides and the like.

US 2012121621 document relates to synergistic compositions comprising prebiotic components selected from the fructose polymers $GF_n$ and $F_m$, either containing a terminal group glucose (G), or without a terminal glucose group, and one or more components of a group of prebiotics consisting of modified starch and partial hydrolysates thereof, partially hydrolyzed inulin, natural oligofructoses, Fructooligosaccharides (FOS), lactulose, galactomannan and suitable partial hydrolysates thereof, indigestible polydextrose, acemannan, several gums, nondigestible dextrin and partial hydrolysates thereof, trans-galacto-oligosaccharides (GOS), xylo-oligosaccharides (XOS), beta-glucan and partial hydrolysates thereof, together, if desired, with phytosterol/phytoestanol components and their suitable esters and, if desired, other plant extracts, mineral components, vitamins and additives.

Many products of the prior art are presented as compositions, which relate to the use of several prebiotics in an alternative manner. For example, a specific composition may contain FOS or GOS or MOS. And not cumulatively, as for example, a composition containing FOS and GOS and MOS.

Many products of the prior art are presented as compositions which represent product with consequent characterizations of the type of process of obtaining the prebiotic, with type of raw material (sugar cane, or maize, or agave, or rice), type of yeast and enzymes employed, different, as well as process conditions like temperature, fermentation time, additives employed etc., also different from each other.

Generic prebiotic terms, such as FOS, MOS, GOS etc., hide complexities in their compositions, and are rarely pure. And even pure, several polymers carry the generic name of the group to which they belong, as is the case of lactulose and of the lactose itself, which are called by the man of the art as being GOS. Apart from this, the man of the art calls FOS a product as if it was a simple compound and not a complex mixture of polymers, and still of different origins, and make comparisons of its performances against the microorganisms in general, not considering that the MOS by example, has better action on bacteria with fimbria type 1, beta-glucans serve to stimulate phagocytosis, and FOS and GOS have bifidogenic effects. The effects of FOS, MOS, GOS, and Beta-glucans cannot be compared linearly, neither individually nor with each other.

Apart from this, FOS often comprises in its MOS formulation, due to its own process of obtaining (mannan-oligosaccharides originating from the cell walls of the yeast used to obtain the FOS).

The most limiting factor for the industry is the price of the prebiotic to be used, which makes it impossible to use as a replacement for antibiotics and organic acids, which are much cheaper, and present good efficiency, but cause the development of resistance by bacteria. In addition, to side effects for animals, such as chronic headaches and heartburn, and humans as antibiotic-resistant bacteria.

Objectives of the Invention

A composition was developed for use as an animal feed growth-promoting additive, which would present the following properties or advantages:

A—had in its formulation specific amounts of prebiotics: with distinct modes of action to be able to act on several fronts in the broad spectrum of bacteria of the animal microbiota, and to present comparable or superior efficiency to that of the growth-promoting antibiotics;

B—Represented an intestinal microbiota modulating product: containing a certain diversity of prebiotic types, capable of having synergy between them, which had a strong growth promoting and reducing the effect on the population of undesirable bacteria, especially the different *Salmonella* and *E. coli* species and serotypes, acting on 5 simultaneous fronts:
    stimulating the immune system;
    causing the agglutination of bacteria with fimbriae type 1;
    promoting their competitive exclusion from undesirable bacteria;
    increasing the production of short-chain organic acids in the cecum;
    increasing the production of protective mucus and villi of the intestinal wall.

C—Were efficient in the long term: since the current strategies of antibiotics and their substitutes are based on the use of a single bactericidal substance, which is not efficient in the long term, as there is a selection of resistant subjects to these substances, in the organisms that make up the intestinal microbiota.

D—Had a low final cost for use in animal nutrition: the most important is that the composition used prebiotics and proportions that would allow its final cost, for large-scale employment in the animal feed industry.

BRIEF DESCRIPTION OF THE INVENTION

Prebiotic, immunomodulatory and growth promoter composition and population control of undesirable bacteria from the intestinal microbiota, particularly animal, were developed with effects analogous to those of growth-promoting antibiotics, but with different mechanisms of action, comprising the following components indicated below:
(a) Fructooligosaccharides (FOS);
(b) Galacto-oligosaccharides (GOS);
(c) Mannan-oligosaccharides (MOS);
(d) 1,3 and 1,6 Beta-glucans.

DETAILED DESCRIPTION OF THE INVENTION

The immunomodulatory and growth promoter composition and control of the undesirable bacterial populations of the intestinal microbiota in animals (including the different species and serotypes of *Salmonella* and *E. coli*, has a growth promoting effect analogous or superior to that of the growth-promoting antibiotics used for this (GPAs). Each component of the composition has a distinct mechanism of action and there is a synergy between these mechanisms of action. The composition is comprised of:
(a) Fructo-oligosaccharides (FOS);
(b) Galacto-oligosaccharides (GOS);
(c) Mannan-oligosaccharides (MOS);
(d) 1,3 and 1,6 Beta-glucans.

According to one embodiment of the invention, the composition comprises the following components:
(a) Fructooligosaccharides (FOS);
(b) Galacto-oligosaccharides (GOS);
(c) Mannan-oligosaccharides (MOS);
(d) 1,3 and 1,6 Beta-glucans;
(e) other prebiotics with bifidogenic action.

For the purposes of this invention, FOS and GOS represent a single component and have the same mechanism of action, which is to produce the bifidogenic effect, i.e., to feed and promote the growth of several species of beneficial bacteria, mainly of the genera *Lactobacillus* and *Bifidobacteria*. The maximum effect of the composition is obtained when FOS and associated GOS are used in their broad sense, i.e., one or more of each of the polymers that make up each of these generic names. Therefore, for the purposes of this invention, there is also provided the composition of Beta-glucans and MOS and [FOS and or GOS]. The composition may still contain other prebiotic components such as lactose, lactulose, inulin, XOS (xylo-oligosaccharides), polydextrose and others with bifidogenic effect.

Bifidogenic prebiotics, which makes up the invention, mostly represented by FOS and GOS, have the purpose of promoting strong populations of *Lactobacillus* and *Bifidobacteria* in the intestinal cecum.

The strong increase in the populations of these beneficial bacteria is aimed at the competitive exclusion of undesirable bacteria, acidifying the fecal bolus in the region of its contact with the intestinal walls, and increasing the production of protective mucus, as well as the quantity and size of the villi intestinal diseases. All these benefits are aimed at improving feed conversion and assisting in the control of undesirable bacteria, especially those of the genera *Salmonella*, *Clostridium* and *E. coli*.

The mechanism of action of mannan-oligosaccharides (MOS) is the agglutination of bacteria with type 1 fimbriae, which are undesirable, such as those of the genera *Salmonella* and *E. coli*, because they adhere the intestinal walls causing enteritis, which prevent an improvement of the feed conversion. A secondary mechanism of action of MOS is the inhibition of the presence of certain fungi, which are equally undesirable for improved feed conversion.

The mechanism of action of 1,3 and 1,6 Beta-glucans is the modulation of the system immunological in general, and especially the one connected to the digestive system, stimulating the multiplication of the macrophages and their phagocytosis activity of the undesirable bacteria that adhere to the intestinal walls or that eventually invade the lymphatic system. Both are undesirable to an improvement in feed conversion.

According to one embodiment of the invention, the composition immunomodulating and growth promoting, and controlling the population of undesirable bacteria of the intestinal microbiota comprises the following essential components:
(a) Fructooligosaccharides (FOS);
(b) Galacto-oligosaccharides (GOS);
(c) Mannan-oligosaccharides (MOS);
(d) 1,3 and 1,6 Beta-glucans;
(e) prebiotics with bifidogenic effects, such as: lactose, lactulose, inulin, XOS (xylos oligosaccharides), polydextrose and other prebiotics with bifidogenic action.

According to another embodiment of the invention, the composition immunomodulating and growth promoting, and controlling the population of undesirable bacteria of the intestinal microbiota comprises the following components:
(a) one or more prebiotics selected from: FOS (Fructooligosaccharides), GOS (Galacto-oligosaccharides), lactose, lactulose, inulin, XOS (Xylo-oligosaccharides), polydextrose and other prebiotics with bifidogenic action;
(b) Mannan-oligosaccharides (MOS);
(c) 1,3 and 1,6 Beta-glucans.

The central thesis of this invention is that there is a synergy between the effects of the prebiotic components of the composition, when used together. The experiment below (Example 1) shows that, in isolation, all components of the composition have growth promoting effects. However, when comparing the growth promoter performance of the invention composition with the individual performances of each of its components, at the same dosage, it is evident that the performance of the composition was higher.

Experiments presented in the examples of compositions according to the invention have shown that the composition of this invention provides better feed conversion rates than growth promoting antibiotics (GPAs) without producing the side effects of the latter. The purpose of this invention is to provide a substitute for the GPAs, which is better suited and which does not have the drawbacks or side effects of the latter.

According to another experiment shown in the examples, the composition according to the invention, also serves as an aid in reducing the population of bacteria of the genus *Salmonella* and *Clostridium*. Currently, these bacteria are controlled by therapeutic antibiotics, most of which are no longer efficient for some species and serotypes of the genus *Salmonella*. This brings increasing risks to human food security. Accordingly, a further purpose of this invention is to assist in controlling the populations of *Salmonella* and *Clostridium* and to increase the efficiency of the therapeutic antibiotics used for that purpose.

The composition may further contain acidifying agents (short-chain organic acids), minerals (in inorganic form or bound to organic molecules), probiotics, tannins, essential oils, etc.

The immunomodulatory and promoter composition for controlling the population of undesirable bacteria of the animal microbiota, according to a preferred embodiment of the invention, comprises the following components:

(a) Fructooligosaccharides (FOS) with short chain polymers and/or Galacto-oligosaccharides (GOS);
(b) Mannan-oligosaccharides (MOS) extracted from *Saccharomyces cerevisae*;
(c) 1,3 and 1,6 Beta-glucans extracted from *Saccharomyces cerevisae*,
(d) other prebiotics with bifidogenic effect.

The FOS or Fructooligosaccharides of the composition of this invention should be, preferably of the type containing only short-chain polymers, which have a higher bifidogenic effect, i.e., comprising GF2, GF3, and GF4. Preferably, these are derived from the fermentation and biotransformation of sugarcane sucrose by enzymes produced by yeasts of the genus *Aureobasidium*. Although not preferably other types of FOS extracted from plants or products from the enzymatic transformation of other sugars by other species of yeast or bacteria may also be used as FOS component of the composition of this invention.

GOS or Galacto-oligosaccharides of the composition of this invention are responsible for reinforcing the bifidogenic effect of FOS, since the combination of the two shows a greater bifidogenic effect than one of each of them alone. In this case, all galactose polymers, whether linked to glucose or not, including lactulose and lactose, are included within the scope of this invention. For the purposes of this invention, GOS should preferably be derived from the enzymatic transformation of cow's milk lactose. Although not preferentially, other types of GOS can also be used, such as those obtained with lactose from the milk of other species, or by biotransformation of bacteria or yeasts, and even by chemical isomerization of lactose. In addition, for purposes of this invention, in compositions intended for non-mammalian nutrition (poultry, swine, and fish), lactose can be used as GOS, although it has a proportionally less bifidogenic effect than the other types of GOS.

MOS or Mannan-oligosaccharides of the composition of this invention are responsible for the agglutination of bacteria with type 1 fimbriae and must come from yeast cell walls of the genera *Saccharomyces* or *Candida*. Preferably, from *Saccharomyces cerevisiae* from the production of ethanol from sugarcane. For the purposes of this invention, preferably, MOS must be extracted from the hydrolysis promoted by the action of commercial proteases added on *Saccharomyces cerevisae* yeasts. Although not preferentially, other types of MOS originating from other species of yeast and obtained by other extraction processes, may also be used in the composition of this invention. Including MOS contained in whole dry yeasts and non-hydrolyzed cell walls of yeasts in general, produced in different musts, whether in primary or secondary fermentation.

Beta-glucans of the composition of this invention are responsible for the stimulation of the immune system and must be derived from the yeast cell wall extraction of the genera *Saccharomyces* or *Candida*, preferably *Saccharomyces cerevisiae*, from the sugar cane ethanol production. For the purposes of this invention, the preferred process of extraction and fractionation of Beta-glucans is based on the use of commercial proteases and beta-glucanases added on yeasts of *Saccharomyces cerevisae*, derived from the production of sugarcane ethanol. Although not preferable, 1,3 and 1,6 Beta-glucans from primary or secondary fermentation of other types of must, from other species and extracted by other processes, including non-enzymatic processes, may also be used in the composition of this invention.

Also with the same immunomodulating and controlling function of the population of undesirable bacteria of the intestinal microbiota, the composition according to the invention may contain mineral micronutrients, in inorganic forms or associated with organic molecules, preferably Chelated Zinc and Copper and Organic Selenium, of which the action is immunomodulatory.

The composition according to the invention contains prebiotics in proportions or contents studied to obtain, at the end, a product which has the greatest efficacy in controlling the population of undesirable bacteria, including those with type 1 fimbriae, such as *Salmonella* and *E coli* species and serotypes, using components of varying costs and origins, but that determined a competitive value for the final product, to the point of being a solution for the substitution of antibiotics currently used as growth promoters in animal feeds or even organic acids, which cause acidity in the intestinal tract and discomfort in animals.

The maximum and minimum mass contents in relation to the total mass of the composition among the pure components are shown in Table 1 below:

TABLE 1

|  | 1,3 and 1,6 Beta-glucans | MOS | GOS (*) | FOS (*) |
| --- | --- | --- | --- | --- |
| Minimum Content | 5% | 3% | 3% | 3% |
| Maximum Content | 20% | 11% | 45% | 80% |

(*) For the purposes of this invention, FOS and GOS are interchangeable. For example, a minimum content of 3% GOS can be obtained by a composition with 1% GOS and 2% FOS. Or, by a composition with 3% FOS.

According to a preferred embodiment of the invention, the contents of the pure components are set forth in Table 2 below:

TABLE 2

|  | 1,3 and 1,6 Beta-glucans | MOS | GOS (*) | FOS (*) |
| --- | --- | --- | --- | --- |
| Minimum Content | 7% | 4% | 9% | 9% |
| Maximum Content | 16% | 8% | 20% | 24% |

(*) For the purposes of this invention, FOS and GOS are interchangeable. For example, a minimum content of 9% GOS can be obtained by a composition with 4% GOS and 5% FOS. Or, by a composition with 9% FOS.

According to another embodiment of the invention, mass ratios between pure, 1,3 and 1,6 Beta-glucans:MOS:GOS:FOS components may range from 1,1 to 2,0 of 1,3 and 1,6 Beta-glucans; 0,5 to 1,0 MOS; from 1,1 to 3,5 GOS and 1,0 to 4,0 FOS. Preferably, the mass ratio between the components of the blend is: from 1,2 to 1,8 of 1,3 and 1,6 Beta-glucans; 0,6 to 0,9 MOS; from 2,0 to 3,5 GOS and 1,5 to 3,8 FOS. Also, more preferably, the mass ratios between 1,3 and 1,6 Beta-glucans:MOS:GOS:FOS follows the ratio 2:1:3:3, in whole numbers. Table 3 below shows these proportions.

TABLE 3

(Beta-glucan Ratios: MOS:GOS:FOS)

| | 1,3 and 1,6 Beta-glucans | MOS | GOS (*) | FOS (*) |
|---|---|---|---|---|
| Preferential | 1.1 to 2.0 | 0.5 to 1.0 | 1.0 to 3.5 | 1.0 to 4.0 |
| More Preferential | 1.2 to 1.8 | 0.6 to 0.9 | 2.0 to 3.5 | 1.5 to 3.8 |
| Much More Preferential | 2 | 1 | 3 | 3 |

The proportions of 1,3 and 1,6 Beta-glucans:MOS:FOS:GOS may change in the composition, subject matter of this invention, according to the type of animal production and the purpose for which it will be destined. For this reason, it is important to establish the correct ranges.

The composition of this invention is indicated to be used as an inclusion rate of 1.5 to 5.0 kg/t of feed, depending on the type of animal production and the purpose of its use. Therefore, one way of evaluating the presence of the composition or the respect to the maximum and minimum limits established above is through the contents of its pure components in the animal feed. Table 4 below shows the limit levels of the composition components in the animal feed.

TABLE 4

(Feeds in Rations, in g Component/t Ration)

| | 1,3 and 1,6 Beta-glucans | MOS | GOS (*) | FOS (*) |
|---|---|---|---|---|
| Preferential | 75 to 1000 | 45 to 550 | 45 to 2250 | 45 to 4000 |
| More Preferential | 105 to 800 | 60 to 400 | 135 to 1000 | 135 to 1200 |
| Much More Preferential | 400 | 210 | 500 | 550 |

Among the different types of animal production to which the composition is intended for, we can mention: chicken, laying hens, pigs, fish, pets etc.

The examples below are merely illustrative of the invention, shall not be construed for limiting effects thereof.

Example 1

A composition, according to the invention, has been developed for comparison with other growth promoting additives, which employed the starting materials indicated in Table 5 below:

TABLE 5

Composition of Example 1

| Raw materials | Mass Components | Mass Composition Contents |
|---|---|---|
| YES GlucanMOS | 24% of 1,3 and 1,6 Beta-glucans and 13% of MOS | 50% |
| YES FOS 60 | 60% FOS | 5% |
| YES GOS 38 | 38% GOS | 45% |

The final composition presented mass contents of the components, according to the invention, in the final composition, as shown in Table 6 below:

TABLE 6

Component Contents of Example 1

| Raw Material Content | 1,3 and 1,6 Beta-glucans | MOS | FOS | GOS |
|---|---|---|---|---|
| 50% of YES GlucamMOS | 12.0% | 6.5% | | |
| 5% of YES FOS 60 | | | 3.0% | |
| 35% of YES GOS 38 | | | | 17.1% |
| Total | 12.0% | 6.5% | 3.0% | 17.1% |

The composition of Example 1 was tested in broilers as a growth promoter additive and its performance was compared to that of a growth-promoting antibiotic from a composition with only Beta-glucans and Manans, and a composition with only FOS and GOS.

A total of 1,250 male broiler chicks of the Cobb lineage were used. The birds were distributed in 5 treatments, with 10 replicates of 25 birds each.

The treatments tested were as follows:

T1—Basal Diet WITHOUT GPA (negative control—NC)

T2—Basal Diet WITH GPA (positive control—PC)—Surmax—(50 g/t)

T3—NC+YES GlucanMOS—(2 kg/t)

T4—NC+YES FOS 60—(0.2 kg/t)+YES GOS 38—(1.8 kg/t)

T5—NC+Combination of Example 1—(2 kg/t)

The results obtained with the treatments were as shown in Table 7 below:

TABLE 7

Treatment Results

| Treatments | Total Glucans (BG + MOS) in g/t of feed | FOS in g/t of feed | GOS in g/t of feed | FOS + GOS in g/t of feed | Feed Conversion |
|---|---|---|---|---|---|
| T1-Without GPA | 0 | 0 | 0 | 0 | 1.86 |
| T2-With GPA | 0 | 0 | 0 | 0 | 1.81 |
| T3-GlucanMOS | 600 | 0 | 0 | 0 | 1.81 |
| T4-FOS + GOS | 0 | 120 | 684 | 804 | 1.81 |
| T5-Example 1 | 300 | 60 | 342 | 402 | 1.79 |

From the results of the experiment shown in Table 7 above, it can be concluded that all of the additives worked. GPA, the composition containing only 1,3 and 1,6 Beta-glucans and MOS (GlucanMOS) and the composition containing only FOS and GOS had similar performance in terms of feed conversion. The composition of Example 1, according to the invention, showed superior performance to all the other treatments. As the same dosage of the prebiotic additives tested was used, i.e., 2 kg/t were used in the feed composition with only 1,3 and 1,6 Beta-glucans and MOS (T3), in the composition with only FOS and GOS (T4) and of the composition according to the invention, with 1,3 and 1,6 Beta-glucans and MOS and FOS and GOS (T5), it can be concluded that there was a synergy between Beta-glucans, MOS, FOS and GOS, when used in a single composition, if compared to the performance of these components alone.

Example 2

A composition according to the invention has been developed to be compared with the growth promoter antibiotic employing the raw materials indicated in Table 8 below:

TABLE 8

Composition of Example 2

| Raw materials | Mass Components | Mass Composition Contents |
|---|---|---|
| Saccharomyces cerevisae (Yeast cell walls) | 24% of 1,3 and 1,6 Beta-glucans and 13% of MOS | 30% |
| Saccharomyces cerevisae autolyzed yeast | 22% of 1,3 and 1,6 Beta-glucans and 14.5% of MOS | 15% |
| YES FOS 60 | 60% FOS | 20% |
| YES GOS 28 | 28% GOS | 35% |

The final composition had mass contents of the components according to the invention in the final composition, as shown in Table 9 below:

TABLE 9

Component Contents of Example 2

| Raw Material Content | 1,3 and 1,6 Beta-glucans | MOS | FOS | GOS |
|---|---|---|---|---|
| 35% Yeast Cell Wall | 7.2% | 3.9% | | |
| 25% Autolyzed Yeast | 3.3% | 2.2% | | |
| 25% YES FOS 60 | | | 12% | |
| 15% YES GOS 38 | | | | 9.8% |
| Total | 10.5% | 6.1% | 12.0% | 9.8% |

Example 3

A composition according to the invention has been developed which employed the raw materials indicated in Table 10 below:

TABLE 10

Composition of Example 3

| Raw materials | Components in Mass | Composition Mass Contents |
|---|---|---|
| YES GlucanMOS | Beta-glucans and 11% MOS | 50% |
| Whey Permeate | 81% Lactose, which is equivalent to 40% GOS | 15% |
| YES FOS 60 | 60% FOS | 25% |
| YES GOS 50 | 50% GOS | 10% |

The final composition presented mass contents of the components according to the invention in the final composition, as shown in Table 11 below:

TABLE 11

Component Contents of Example 3

| Raw Material Content | 1,3 and 1,6 Beta-glucans | MOS | FOS | GOS |
|---|---|---|---|---|
| 50% YES GlocanMOS | 12.0% | 5.5% | | |
| 15% Whey Permeate | | | | 9.0% |
| 25% YES FOS 60 | | | 12.5% | |
| 10% YES GOS 50 | | | | 4.0% |
| Total | 12.0% | 5.5% | 9.0% | 16.5% |

Formulations of examples 2 and 3 were administered to commercial broiler chickens, with an inclusion of 2 kg per ton of feed. The results are shown in Tables 12 (Diets with Zinc Bacitracin Antibiotic, As Growth Promoter Additives), 13 (Diets with the Composition of Example 2, as Growth Promoter Additives) and 14 (Diets with the Composition of Example 3, As Growth Promoter Additive) below.

TABLE 12

Results of Treatments with Antibiotic (**)

| | Final Average Body Weight (kgBW/bird) | Food Intake (kg/Bird) | Feed Conversion | Control of Salmonella (*) |
|---|---|---|---|---|
| Production 1 | 3.14 | 5.329 | 1.72 | 100 |
| Production 2 | 3.07 | 5.167 | 1.71 | 100 |
| Production 3 | 3.20 | 5.034 | 1.60 | 100 |
| Production 4 | 3.01 | 5.105 | 1.72 | 100 |
| Average | 3.11 | 5.159 | 1.69 | 100 |

TABLE 13

Results of Treatments with Composition of Example 2

| | Final Average Body Weight (kgBW/bird) | Food Intake (kg/Bird) | Feed conversion | Control of Salmonella (*) |
|---|---|---|---|---|
| Production 1 | 3.21 | 5.232 | 1.66 | 99 |
| Production 2 | 2.98 | 5.096 | 1.74 | 95 |
| Production 3 | 3.11 | 4.928 | 1.61 | 102 |
| Production 4 | 3.07 | 5.088 | 1.68 | 107 |
| Average | 3.09 | 5.086 | 1.67 | 101 |

TABLE 14

Results of Treatments with Composition of Example 3

| | Final Average Body Weight (kgBW/hird) | Food Intake (kg/Bird) | Feed Conversion | Control of Salmonella (*) |
|---|---|---|---|---|
| Production 1 | 3.27 | 5.298 | 1.65 | 101 |
| Production 2 | 3.07 | 5.123 | 1.70 | 97 |
| Production 3 | 3.21 | 5.102 | 1.61 | 102 |
| Production 4 | 3.10 | 5.099 | 1.67 | 105 |
| Average | 3.16 | 5.156 | 1.66 | 101 |

Note:

(*)—*Salmonella* Control Efficiency Index, measured by conducting a 'propé' [shoe covers] drag swab tests. Antibiotic=100

(**)—Zinc Bacitracin

Test results with compositions of Example 2 and 3, with growth promoting additives in broiler chicken feeds shown in tables 12, 13 and 14 above, show that the treatments containing the compositions of Examples 2 and 3, according to the invention, had better results than treatments containing antibiotics as growth promoters and even in the control of *Salmonella*. Although the final body weight of the animals treated with the composition of Example 2 was slightly lower than those of those treated with an antibiotic.

Example 4

A composition, according to the invention, has been developed, which employed the raw materials indicated in Table 15 below:

TABLE 15

| Composition of Example 4 | | |
|---|---|---|
| Raw materials | Mass Components | Composition Mass Contents |
| *Saccharomyces cerevisae* yeast cell wall | 24% of 1,3 and 1,6 Beta-glucans and 13% of MOS | 30% |
| *Saccharomyces cerevisae* Autolyzed yeast | 22% of 1,3 and 1,6 Beta-glucans and 14,5% of MOS | 25% |
| Ingredion FOS 95 | 95% FOS | 25% |
| YES GOS 38 | 38% GOS | 20% |

The final composition showed mass contents of the components on the final composition, according to the invention, as Table 16 below:

TABLE 16

| Component Contents of Example 4 | | | | |
|---|---|---|---|---|
| Raw Material Content | 1.3 and 1.6 Beta-glucans | MOS | FOS | GOS |
| 35% Yeast Cell Wall | 7.2% | 3.9% | | |
| 25% Autolyzed Yeast | 5.5% | 3.6% | | |
| 25% YES FOS 60 | | | 23.7% | |
| 15% YES GOS 38 | | | | 7.6% |
| Total | 12.7% | 7.5% | 23.7% | 7.6% |

Composition of Example 4 was tested in piglets to evaluate their performance ratio in comparison with growth promoter antibiotic (GPA) and with sodium butyrate. All were added to the rations of the respective treatments as growth promoting additives.

Sixty-three piglets were weaned at 22 days of age, with a start average body weight of 5.48 kg, both sexes, PIC genetics. The animals were separated by sex and distributed into 3 treatments, with 7 replicates of 3 animals each, during the whole period (22 to 64 days of age). Diet was formulated without Zinc Oxide or any other antimicrobial.

The treatments were:

T1: Basal Diet+GPA (colistin 8%—40 ppm)

T2: Basal Diet+Sodium Butyrate 30% (1 kg/t)

T3: Basal Diet+Composition of the Invention of Example 4 (2 kg/t)

The results were as follows:

TABLE 17

| Performance | | | |
|---|---|---|---|
| | APC | Butyrate | Example 4 |
| GDP (g) | 0.25 | 0.73 | 0.24 |
| CA | 1.91 | 2.07 | 1.83 |

GDP = daily gain in grams/animal/day

CA = feed conversion

Results of Table 17 above show that the composition of Example 4, according to the invention, showed much higher feed conversion (CA) performance than the growth promoting antibiotic and Na-butyrate. Although there was no statistically significant difference between the daily body weight gains of the treatments.

TABLE 18

| Diarrhea index | | | |
|---|---|---|---|
| | APC | Butyrate | Example 4 |
| Grade I | $21^b$ | $22^b$ | $8^a$ |
| Grade II | $36^b$ | $33^{ab}$ | $23^a$ |
| Grade III | $63^b$ | $53^b$ | $40^a$ |

Results of Table 18 above show that the composition of Example 4 was much higher than the antibiotic (GPA) and Na-butyrate to control diarrhea of the piglets. Signal that was more efficient as a tool to control the undesirable bacteria, which explains the better feed conversion.

TABLE 19

| Fatty acids in Cecum | | | |
|---|---|---|---|
| | APC | Butyrate | Example 4 |
| Acetic | 0.32 | 0.38 | 0.38 |
| Propionic | $0.23^b$ | $0.32^a$ | $0.37^a$ |
| Butyric | 0.13 | 0.18 | 0.17 |
| Total | 0.67 | 0.87 | 0.93 |

Results of Table 19 above show that the composition of Example 4 provided a higher production of short chain fatty acids in the pig's cecum. This higher production of short chain fatty acids can also be an explanation for the lower incidence of diarrhea and for the better feed conversion, since it probably reduced intestinal pH, making inhospitable the environment for the undesirable bacteria that cause diarrhea, and increasing the absorption of nutrients.

Examples 5, 6 and 7

Three prebiotic compositions were made according to the invention to be tested as growth-promoting additives in chickens inoculated with *Salmonella enteritidis*. The compositions used the raw materials listed below in Table 20.

TABLE 20

Compositions of Examples 5, 6 and 7

| Raw materials | Mass Components | Example 5: Mass Composition Contents | Example 6: Mass Composition Contents | Example 7: Mass Composition Contents |
|---|---|---|---|---|
| YES GlucanMOS | 24% of 1,3 and 1,6 Beta-glucans and 13% of MOS | 50% | 50% | 50% |
| YES FOS 60 | 60% FOS | 5% | 15% | 25% |
| YES GOS 28 | 28% GOS | 45% | 35% | 25% |

Compositions of examples 5, 6 and 7 showed mass contents of the components on the final composition according to the invention, as Table 21 below:

TABLE 21

Component Contents of Examples 5, 6 and 7

| Treatments | 1.3 and 1.6 Beta-glucans | MOS | FOS | GOS |
|---|---|---|---|---|
| Example 5 | 11.5% | 7.0% | 3.0% | 12.6% |
| Example 6 | 11.5% | 7.0% | 9.0% | 9.8% |
| Example 7 | 11.5% | 7.0% | 15.0% | 7.0% |

Compositions of examples 5, 6 and 7 were used as growth promoting additives for growing chicken feeds, i.e., during the first 28 days of life, to evaluate the productive performance and control of *Salmonella enteritidis*. A total of 300 broilers of the commercial Ross lineage were distributed into 5 treatments with six replicates of 10 animals each. On the fourth day, all birds were inoculated with *Salmonella enteritidis*. Body weight control, feed intake and 'propé' [shoe covers] drag swab were made weekly to evaluate the presence of *Salmonella* in the poultry bed.

The treatments were as follows:

T1: Basal Diet+Antibiotic Fosbac 350—30 mg/t

T2: Basal Diet+YES GlucanMOS—2 kg/t

T3: Basal Diet+Invention Composition of Example 5—2 kg/t

T4: Basal Diet+Composition of the Invention of Example 6—2 kg/t

T5: Basal Diet+Composition of the Invention of Example 7—2 kg/t

The results obtained were as follows:

TABLE 22

Treatment Results

| Treatments | Final Body Weight (g/bird) | Feed intake (g/bird) | Feed Conversion |
|---|---|---|---|
| T1 - Antibiotic | 1,708 | 2,682 | 1.62 |
| T2 - GlucanMOS | 1,754 | 2,666 | 1.56 |
| T3 - Example 5 | 1,729 | 2,559 | 1.52 |
| T4 - Example 6 | 1,755 | 2,580 | 1.51 |
| T5 - Example 7 | 1,733 | 2,634 | 1.57 |

Results of Table 22 above show that the compositions of Examples 5, 6 and 7 were higher in feed conversion (FC), when compared to the performance of the treatment that used an antibiotic. Among the compositions tested, that of Example 6 was the one that showed better feed conversion, confirming that the best performance and the best bifidogenic effect are obtained when similar proportions of FOS and GOS are used.

TABLE 23

Re-isolation of *S. enteritidis* in the poultry bed. Positive tests of 'propé' [shoe covers] drag swab.

| | 1st week | | | | | | 2nd week | | | | | | 3rd week | | | | | | 4th week | | | | | |
|---|---|---|---|---|---|---|---|---|---|---|---|---|---|---|---|---|---|---|---|---|---|---|---|---|
| | R1 | R2 | R3 | R4 | R5 | R6 | R1 | R2 | R3 | R4 | R5 | R6 | R1 | R2 | R3 | R4 | R5 | R6 | R1 | R2 | R3 | R4 | R5 | R6 |
| Antibiotic | | | | | | | | | | | | | | | | | | | | | | | | |
| GlucanMOS | | p | | p | p | p | | | | | | | p | p | p | | | | | p | | | | |
| Example 5 | | p | p | | p | | p | p | p | | | | | p | | | | | | | | | | |
| Example 6 | p | p | p | p | p | p | | p | p | p | p | | | | p | p | | | | p | | | | |
| Example 7 | p | p | p | | | | p | | p | p | p | | | | | | | | | | | | | |

Results in Table 23 above show the rate of reduction of the presence of *Salmonella enteritidis* in the poultry bed of each treatment. Results show that the treatment that used the composition of Example 7 as a growth promoter additive was the one that showed the highest efficiency in eliminating the presence of *Salmonella*. This may be an indication that compositions with higher levels of FOS are the most indicated, when control of *Salmonella* is necessary, in addition to promoting growth.

Example 8, 9 and 10

Three prebiotic compositions were made according to the invention to be tested as growth promoting additives in chickens inoculated with *Salmonella heidelbergii*. The compositions used the raw materials listed below in Table 24.

TABLE 24

Compositions of Examples 8, 9 and 10

| Raw materials | Mass Components | Example 8: Mass Composition Contents | Example 9: Mass Composition Contents | Example 10: Mass Composition Contents |
|---|---|---|---|---|
| YES GlucanMOS | 24% of 1,3 and 1,6 Beta-glucans and 13% of MOS | 50% | 50% | 50% |
| YES FOS 60 | 60% FOS | 5% | 15% | 50% |
| YES GOS 38 | 38% GOS | 45% | 35% | 0% |

Compositions of Examples 8, 9 and 10 showed mass contents of the components of the final compositions, according to the invention, as set forth in Table 25 below:

TABLE 25

Component Content of Examples 8, 9 and 10

| Treatments | 1,3 and 1,6 Beta-glucans | MOS | FOS | GOS |
|---|---|---|---|---|
| Example 8 | 11.5% | 7.0% | 3.0% | 12.6% |
| Example 9 | 11.5% | 7.0% | 9.0% | 9.8% |
| Example 10 | 11.5% | 7.0% | 30.0% | 0.0% |

Compositions of examples 8, 9 and 10 were used as growth promoting additives for growing chicken feeds, i.e., during the first 28 days of life, to evaluate the control of *Salmonella heidelbergii*. On the fourth day of life, 20% of the birds were inoculated with *Salmonella heidelbergii*. At the end of the 28 days, fecal material was collected from the cecum of the birds and the counting of colony forming units (CFUs) of *Salmonella* and sulfite-reducing *Clostridium*.

The treatments were as follows:

T1: Basal Diet+SH Challenge—WITHOUT GPA (growth promoting antibiotic)

T2: Basic Diet+SH+APC Challenge (Enramicima 8 ppm)

T3: Basal Diet+SH Challenge+Sodium Butyrate (1.5 kg/t of feed)

T4: Basal Diet+Composition of the Invention of Example 8—3 kg/t

T5: Basal Diet+Composition of the Invention of Example 9—3 kg/t

T6: Basal Diet+Composition of the Invention of Example 10—3 kg/t

T7: Basal Diet+Composition of the Invention of Example 9—3 kg/t+Probiotic

The results obtained were as follows:

TABLE 26

Results of the Treatments of Example 8, 9 and 10

| Treatments | Total Glucans (*) | FOS (*) | GOS (*) | FOS + GOS (*) | *Salmonella heidelbergii* (CFU/g) | Sulfite-reducing *Clostridium* | Statistic Significance |
|---|---|---|---|---|---|---|---|
| T1-Without GPA | — | — | — | — | 1.96 | 5566 | ab |
| T2-With GPA | — | — | — | — | 1.66 | 5115 | bc |
| T3-Na-Butyrate | — | — | — | — | 1.70 | 4959 | bc |
| T4-Example 8 | 432 | 90 | 513 | 603 | 1.66 | 5138 | bc |
| T5-Example 9 | 432 | 270 | 399 | 669 | 1.68 | 4787 | c |
| T6-Example 10 | 432 | 900 | — | 900 | 1.57 | 4382 | c |
| T7-E9 + Probiotic | 387 | 270 | 399 | 669 | 1.69 | 5943 | ab |

(*)-contents in g/t of feed

Results of Table 26 above show that the compositions of Examples 8, 9 and 10 were as effective in controlling *Salmonella heidelbergii* and sulfite-reducing *Clostridium* as the growth promoter antibiotic (GPA) and Sodium butyrate. Composition 10, which contained the highest concentration of FOS, was the most efficient in the control of *Salmonella* and *Clostridium*, again indicating that compositions, according to the invention, containing higher levels of FOS are more indicated to help to control bacteria of the genera *Salmonella* and *Clostridium*. The addition of probiotics to composition 9 did not help to improve its performance.

Examples 11, 12, 13, 14, 15 and 16

Six prebiotic compositions were made according to the invention to be tested as growth promoting additives in laying hens. The purpose of the test was to compare the performance of formulations containing different types of prebiotics with bifidogenic effect on the productive performance of laying birds. The compositions used the raw materials listed below in Table 27 below:

body weight gain of laying hens was evaluated, together with the weight of their egg production in the period. The experiment used 28 hens containing 118 laying hens each, Lohmann genetics, with 21 weeks of life, distributed in 7 treatments, with 4 replicates each.

The treatments were as follows:
T1—Poultry Basal Diet (without GPAs, butyric acid and essential oils)
T2—BD+3 kg/t of Example 11 (Beta-glucans+MOS+FOS+GOS+Lactose)
T3—BD+3 kg/t of Example 12, (Beta-glucans+MOS+FOS+Lactulose)
T4—BD+3 kg/t of Example 13, (Beta-glucans+MOS+XOS+Lactulose)
T5—BD+3 kg/t of Example 14, (Beta-glucans+MOS+Lactulose+Lactose)
T6—BD+3 kg/t of Example 15, (Beta-glucans+MOS+XOS+Lactose)
T7—BD+3 kg/t of Example 16, (Beta-glucans+MOS+FOS+Lactose)

TABLE 27

Compositions of Examples 11, 12, 13, 14, 15 and 16

| Raw Materials | Mass Components | Example 11: Mass Composition Contents | Example 12: Mass Composition Contents | Example 13: Mass Composition Contents | Example 14: Mass Composition Contents | Example 15: Mass Composition Contents | Example 16: Mass Composition Contents |
|---|---|---|---|---|---|---|---|
| YES GlucanMOS | 24% of 1,3 and 1,6 Beta-glucans and 13% of MOS | 45% | 45% | 45% | 45% | 45% | 45% |
| Ingredion FOS 95 | 60% FOS | 15% | 25% | | | | 20% |
| YES GOS 38 | 38% GOS | 25% | | | | | |
| Lactulose 25 | 25% Lactulose | | 30% | 30% | 25% | | |
| XOS 95 | 95% of XOS | | | 25% | | 20% | |
| Whey Permeate | 81% of Lactose is equivalent to 40% of GOS | 15% | | | 30% | 35% | 35% |

Compositions of examples 11, 12, 13, 14, 15 and 16 showed mass contents (g/kg of composition) of the components of the compositions, according to the invention, as shown in Table 28 below:

TABLE 28

Component Contents of Examples 11, 12, 13, 14, 15 and 16 (g/kg)

| | 1,3 and 1,6 Beta glucans | MOS | FOS | GOS equivalent to (*) | XOS | Bifidogenic Totals |
|---|---|---|---|---|---|---|
| Example 11 | 104 | 63 | 143 | 155 | — | 298 |
| Example 12 | 104 | 63 | 238 | 42 | — | 280 |
| Example 13 | 104 | 63 | — | 42 | 238 | 280 |
| Example 14 | 104 | 63 | — | 155 | — | 155 |
| Example 15 | 104 | 63 | — | 140 | 190 | 330 |
| Example 16 | 104 | 63 | 190 | 140 | — | 330 |

The different compositions according to the invention were tested with laying hens, in a commercial farm, under a system of production according to the rules of the organic system, i.e., without the use of antibiotics, either as growth promoters or therapies. The compositions tested had among their components several types of bifidogenic prebiotics, which are FOS, GOS, XOS, Lactulose. and Lactose. The purpose of this experiment was to evaluate the performance of several dosages and combinations of these prebiotics in relation to the feed conversion of laying hens in the first 150 days of production. To calculate the feed conversion, the Results obtained are those shown in Tables 29, 30, 31, 32 and 33 below:

TABLE 29

Average body weights of laying hens (BW grams/laying hen)

| | Initial | 1 to 30 d | 31 to 60 d | 61 to 90 d | 91 to 120 d | 121 a150 d | Final |
|---|---|---|---|---|---|---|---|
| Control | 1,453 | 1,505 | 1,625 | 1,765 | 1,848 | 1,856 | 1,859 |
| Example 11 | 1,463 | 1,555 | 1,669 | 1,802 | 1,878 | 1,878 | 1,877 |
| Example 12 | 1,447 | 1,537 | 1,654 | 1,793 | 1,866 | 1,862 | 1,868 |
| Example 13 | 1,441 | 1,538 | 1,654 | 1,784 | 1,866 | 1,872 | 1,873 |
| Example 14 | 1,475 | 1,528 | 1,646 | 1,781 | 1,861 | 1,860 | 1,856 |
| Example 15 | 1,465 | 1,534 | 1,641 | 1,783 | 1,861 | 1,865 | 1,864 |
| Example 16 | 1,444 | 1,552 | 1,662 | 1,791 | 1,872 | 1,871 | 1,872 |

TABLE 30

Average Weights of Eggs (g/egg)

| | 0 to 30 d | 31 to 60 d | 61 to 90 d | 91 a120 d | 121 a150 d | Average |
|---|---|---|---|---|---|---|
| Control | 47.0 | 53.5 | 57.0 | 60.2 | 61.0 | 57.1 |
| Example 11 | 48.0 | 54.4 | 57.9 | 61.2 | 62.1 | 58.0 |

TABLE 30-continued

Average Weights of Eggs (g/egg)

|  | 0 to 30 d | 31 to 60 d | 61 to 90 d | 91 a120 d | 121 a150 d | Average |
|---|---|---|---|---|---|---|
| Example 12 | 47.3 | 53.9 | 57.4 | 60.9 | 61.8 | 57.6 |
| Example 13 | 47.5 | 54.1 | 57.3 | 61.0 | 61.8 | 57.7 |
| Example 14 | 47.3 | 53.7 | 57.4 | 60.5 | 61.3 | 57.4 |
| Example 15 | 47.4 | 53.9 | 57.5 | 60.6 | 61.6 | 57.5 |
| Example 16 | 47.8 | 54.4 | 57.7 | 61.3 | 61.9 | 57.9 |

TABLE 31

Eggs Produced (units)

|  | 0 to 30 d | 31 to 60 d | 61 to 90 d | 91 a120 d | 121 a150 d | Total |
|---|---|---|---|---|---|---|
| Control | 1,278 | 2,628 | 3,096 | 3,240 | 3,276 | 13,518 |
| Example 11 | 1,409 | 2,731 | 3,207 | 3,338 | 3,374 | 14,049 |
| Example 12 | 1,356 | 2,694 | 3,177 | 3,296 | 3,353 | 13,876 |
| Example 13 | 1,358 | 2,704 | 3,164 | 3,312 | 3,361 | 13,899 |
| Example 14 | 1,326 | 2,694 | 3,181 | 3,306 | 3,333 | 13,840 |
| Example 15 | 1,346 | 2,693 | 3,152 | 3,301 | 3,332 | 13,824 |
| Example 16 | 1,399 | 2,709 | 3,196 | 3,330 | 3,364 | 13,998 |

TABLE 32

Feed intake (kg)

|  | 0 to 30 d | 31 to 60 d | 61 to 90 d | 91 a120 d | 121 a150 d | Total |
|---|---|---|---|---|---|---|
| Control | 386 | 417 | 452 | 474 | 476 | 2,204 |
| Example 11 | 390 | 409 | 439 | 463 | 466 | 2,166 |
| Example 12 | 399 | 423 | 462 | 483 | 479 | 2,247 |
| Example 13 | 397 | 425 | 461 | 483 | 477 | 2,244 |
| Example 14 | 398 | 428 | 456 | 477 | 481 | 2,240 |
| Example 15 | 395 | 427 | 452 | 477 | 478 | 2,229 |
| Example 16 | 393 | 422 | 416 | 463 | 473 | 2,167 |

TABLE 33

Feed conversion of Examples 11, 12, 13, 14, 15 and 16

|  | 0 to 30 d | 31 to 60 d | 61 to 90 d | 91 to 120 d | 121 to 150 d | Final |
|---|---|---|---|---|---|---|
| Control | 5.82 | 2.69 | 2.34 | 2.31 | 2.37 | 2.69 |
| Example 11 | 4.95 | 2.52 | 2.18 | 2.18 | 2.23 | 2.51 |
| Example 12 | 5.33 | 2.66 | 2.32 | 2.31 | 2.32 | 2.64 |
| Example 13 | 5.22 | 2.65 | 2.34 | 2.28 | 2.29 | 2.63 |
| Example 14 | 5.77 | 2.70 | 2.29 | 2.28 | 2.36 | 2.67 |
| Example 15 | 5.48 | 2.70 | 2.28 | 2.28 | 2.32 | 2.64 |
| Example 16 | 4.92 | 2.63 | 2.08 | 2.16 | 2.27 | 2.51 |

Results shown in the tables above show that all the prebiotic compositions tested were efficient as promoters of conversion improvement production performance of laying hens. However, the compositions of the Examples 11 and 16, which were formulated with FOS and GOS, were much more than those formulated with other types of prebiotics with a bifidogenic effect. That confirms that the preferred composition of this invention, which is Beta-glucans+MOS+FOS+GOS is the one with the best synergy and the highest economic efficiency. The results also showed that, for this experiment with laying hens, GOS 38 was more efficient than Lactose, because the composition of the T2 treatment, with the composition of Example 11 contained only 298 g/kg of total bifidogenic prebiotics, while that of the T7 treatment, with the composition of Example 16, contained a total of 330 g/kg. And there was no statistically significant difference between treatments.

Example 17, 18 and 19

Three prebiotic compositions were made according to the invention to be tested as growth promoting additives in pigs. The purpose of the test was to compare the efficiency of formulations containing different levels of FOS and Beta-glucans in the substitution of growth-promoting antibiotics. The compositions used the raw materials listed below in Table 34 below:

TABLE 34

Compositions of Example 17, 18 and 19

| Raw materials | Mass Components | Example 17: Mass Composition Contents | Example 18: Mass Composition Contents | Example 19: Mass Composition Contents |
|---|---|---|---|---|
| YES GlucanMOS | 24% of 1,3 and 1,6 Beta-glucans and 13% of MOS | 50% | 50% | 50% |
| YES FOS 60 | 60% FOS | 45% | 35% | 25% |
| YES GOS 38 | 38% GOS | 5% | 15% | 25% |

Compositions of examples 17, 18 and 19 showed mass contents of the components of the final compositions according to the invention, as set forth in Table 35 below:

TABLE 35

Component Content of Examples 17, 18 and 19

| Treatments | 1,3 and 1,6 Beta-glucans | MOS | FOS | GOS |
|---|---|---|---|---|
| Example 17 | 11.5% | 7.0% | 30.0% | 2.5% |
| Example 18 | 11.5% | 7.0% | 21.0% | 7.0% |
| Example 19 | 11.5% | 7.0% | 15.0% | 11.4% |

For 41 days the compositions were tested on 120 PIC genetics piglets, separated into batches of males and females, weaned at 21 days. Were tested 5 treatments, with 6 replicates each, in 4 animal bays.

The treatments were as follows:
T1—Basal Diet+addition of Halquinol, as growth promoting antibiotics.
T2—Basal Diet+2 kg/t from YES GlucanMOS
T3—Basal Diet+2 kg/t of the composition of Example 17
T4—Basal Diet+2 kg/t of the composition of Example 18
T5—Basal Diet+2 kg/t of the composition of Example 19.
Results obtained were those shown in Tables 36, 37 and 38 below:

TABLE 36

Results of the First 15 days

| Treatments | Daily Feed Intake (g/head) | Daily Body Weight Gain (g/head) | Feed Conversion |
|---|---|---|---|
| Antibiotic | 309 | 243 | 1.28 |
| Yes GlucanMOS | 301 | 211 | 1.46 |
| Example 17 | 305 | 241 | 1.27 |

TABLE 36-continued

Results of the First 15 days

| Treatments | Daily Feed Intake (g/head) | Daily Body Weight Gain (g/head) | Feed Conversion |
|---|---|---|---|
| Example 18 | 325 | 239 | 1.37 |
| Example 19 | 332 | 249 | 1.38 |

TABLE 37

Results of the First 28 days

| Treatments | Daily Feed Intake (g/head) | Daily Body Weight Gain (g/head) | Feed Conversion |
|---|---|---|---|
| Antibiotic | 535 | 343 | 1.56 |
| Yes GlucanMOS | 514 | 322 | 1.60 |
| Example 17 | 531 | 345 | 1.54 |
| Example 18 | 563 | 347 | 1.63 |
| Example 19 | 573 | 356 | 1.61 |

TABLE 38

Results of the 41 days of the Experiment

| Treatments | Daily Feed Intake (g/head) | Daily Body Weight Gain (g/head) | Food Conversion |
|---|---|---|---|
| Antibiotic | 719 | 413 | 1.74 |
| Yes GlucanMOS | 708 | 399 | 1.78 |
| Example 17 | 714 | 401 | 1.78 |
| Example 18 | 720 | 394 | 1.83 |
| Example 19 | 748 | 411 | 1.82 |

Results shown in tables 36, 37 and 38 above show that the composition of Example 17 which contained higher FOS content was as efficient as that of the growth-promoting antibiotics. Probably, a higher inclusion rate of 3 kg/t of feed would have shown a much higher performance than the growth promoting antibiotics.

Compositions of examples 18 and 19 showed lower performances, probably due to the lactose content that is part of the constitution of YES GOS 38 used as a component. Pigs, being mammals, produce lactase. Therefore, lactose has no bifidogenic effect, which impaired the performance of those compositions.

The invention claimed is:

1. A feed additive comprising in weight, in relation to the total mass of the composition:
    (a) 9% to 24% of pure FOS (Fructooligosaccharides);
    (b) 9% to 20% of pure GOS (Galactooligosaccharides);
    (c) 4% to 8% of pure MOS (Mannan-oligosaccharides); and
    (d) 7% to 16% of pure 1,3 and 1,6 beta-glucans,
    wherein the percentages are in relation to the total mass of the composition.

2. The feed additive composition of claim 1 comprising a ratio of beta-glucans:MOS:GOS:FOS by weight, relative to total mass of the composition, varying from:
    (a) 1.5 to 3.8 of pure FOS;
    (b) 2.0 to 3.5 of pure GOS;
    (c) 0.6 to 0.9 of pure MOS; and
    (d) 1.2 to 1.8 of pure 1,3 and 1,6 beta-glucans.

3. The feed additive composition of claim 1 comprising a ratio of pure beta-glucans:MOS:GOS:FOS by weight, relative to total mass of the composition, in the ratio of 2:1:3:3, when expressed in whole numbers.

4. The feed additive composition of claim 1, wherein the composition further contains mineral micronutrients in inorganic, organic or chelated form.

5. The feed additive composition of claim 4, wherein the composition further contains chelated zinc, copper and organic selenium.

6. The feed additive composition of claim 1, wherein the composition further comprises lactose, lactulose, inulin, xylo oligosaccharide (XOS) and butyric acid derivatives.

7. A method to treat *Salmonella*, *E. coli* and/or *Clostridium* in an animal comprising administering the composition of claim 1 to animals so as to treat said *Salmonella*, *E. coli* and/or *Clostridium*.

* * * * *